United States Patent
Kinsho et al.

(10) Patent No.: US 9,725,400 B2
(45) Date of Patent: Aug. 8, 2017

(54) (E)-2-ISOPROPYL-5-METHYL-3,5-HEXADIENOATE COMPOUND, METHOD FOR PRODUCING THE SAME, AND METHODS FOR PRODUCING (E)-2-ISOPROPYL-5-METHYL-3,5-HEXADIENOL AND (E)-2-ISOPROPYL-5-METHYL-3,5-HEXADIENYL CARBOXYLATE BY USING THE SAME

(71) Applicant: Shin-Etsu Chemical Co., Ltd., Tokyo (JP)

(72) Inventors: Takeshi Kinsho, Joetsu (JP); Naoki Ishibashi, Joetsu (JP); Shinnosuke Wakamori, Joetsu (JP); Miyoshi Yamashita, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/219,655

(22) Filed: Jul. 26, 2016

(65) Prior Publication Data

US 2017/0050913 A1    Feb. 23, 2017

(30) Foreign Application Priority Data

Aug. 18, 2015    (JP) .................. 2015-161019

(51) Int. Cl.
| | |
|---|---|
| *C07C 69/587* | (2006.01) |
| *C07C 29/14* | (2006.01) |
| *C07C 29/147* | (2006.01) |
| *C07C 69/08* | (2006.01) |
| *C07C 67/327* | (2006.01) |
| *C07C 67/40* | (2006.01) |
| *C07C 67/08* | (2006.01) |

(52) U.S. Cl.
CPC ............ *C07C 69/587* (2013.01); *C07C 29/14* (2013.01); *C07C 29/147* (2013.01); *C07C 67/08* (2013.01); *C07C 67/327* (2013.01); *C07C 67/40* (2013.01)

(58) Field of Classification Search
CPC .................................................. C07C 69/587
See application file for complete search history.

(56) References Cited

PUBLICATIONS

Zaragoza Dorwald, Side Reactions in Organic Synthesis, 2005, WILEY-VCH Verlag GmbH & Co. KGaA, Weinheim, Preface. p. IX.*

Wikipedia, Propellane, recovered from https://en.wikipedia.org/wiki/Propellane on Feb. 14, 2017, pp. 1-4.*
Kaufmann et al, Helvetica Chimica Acta, 133. Synthese von d,l,—beta, gamma-Dihydro-lavandulol, 1946, 29(5), pp. 1133-1144, with English translation of relevant passage.*
Extended European Search Report corresponding to European Patent Application No. 16182104.6 (5 pages) (dated Jan. 1, 2017).
Tabeta et al. "A New Lavandulol-related Monoterpene in the Sex Pheromone of the Grey Pineapple Mealybug, *Dysmicoccus neobrevipes*", J. Chem. Ecol. 41:194-201 (2015).
Simon et al. "133. Synthes: von d,l-β,γ-Dihydro-lavandulol" *Helvetica Chimica Acta.* XXIX(V):1133-1144 (1946).

* cited by examiner

*Primary Examiner* — Paul A Zucker
(74) *Attorney, Agent, or Firm* — Myers Bigel, P.A.

(57) ABSTRACT

Provided is a geometrically selective method for producing (±)-(E)-2-isopropyl-5-methyl-3,5-hexadienyl acetate, which is a sex pheromone of grape pineapple mealybug (GPMB). Specifically provided is a method for producing a an (E)-2-isopropyl-5-methyl-3,5-hexadienyl carboxylate compound (4), the method comprising the steps of: dehydrating a 3-hydroxy-2-isopropyl-5-methyl-4-hexenoate compound (1) to obtain an (E)-2-isopropyl-5-methyl-3,5-hexadienoate compound (2); reducing the alkoxycarbonyl group of the compound (2) to obtain (E)-2-isopropyl-5-methyl-3,5-hexadienol (3); and esterifying the compound (3) to obtain the compound (4).

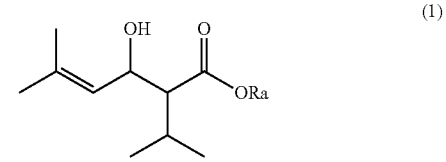

(1)

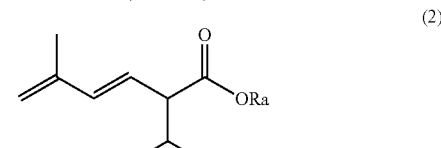

(2)

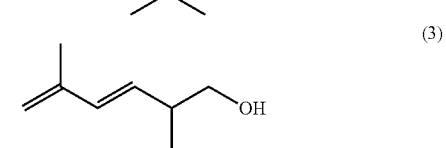

(3)

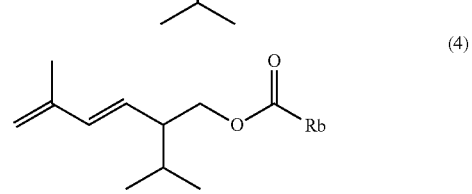

(4)

4 Claims, No Drawings

(E)-2-ISOPROPYL-5-METHYL-3,5-HEXADIENOATE COMPOUND, METHOD FOR PRODUCING THE SAME, AND METHODS FOR PRODUCING (E)-2-ISOPROPYL-5-METHYL-3,5-HEXADIENOL AND (E)-2-ISOPROPYL-5-METHYL-3,5-HEXADIENYL CARBOXYLATE BY USING THE SAME

RELATED APPLICATION

This application claims priority from Japanese Patent Application No. 2015-161019, filed Aug. 18, 2015, the disclosure of which is incorporated by reference herein in its entirety.

FIELD AND BACKGROUND OF THE INVENTION

The present invention relates to an (E)-2-isopropyl-5-methyl-3,5-hexadienoate compound useful as a synthetic perfume or as a synthetic intermediate in organic synthesis; a method for producing the hexadienoate compound; and a method for producing (E)-2-isopropyl-5-methyl-3,5-hexadienol. The present invention also relates to a method for producing an (E)-2-isopropyl-5-methyl-3,5-hexadienyl carboxylate useful as a bioactive substance such as an insect sex pheromone and a substance related therewith. For example, the present invention relates to a method for producing (E)-2-isopropyl-5-methyl-3,5-hexadienyl acetate, which is a sex pheromone of *Dysmicoccus neobrevipes* (generic name: grape pineapple mealybug).

The sex pheromones of insects are biologically active substances that are commonly secreted by female individuals and have the function of attracting male individuals. A small amount of a sex pheromone shows a strong attraction activity. The sex pheromones have been widely used as means for forecasting insect emergence or for ascertaining regional spread (i.e. invasion into a specific area) of the insect pests and as means for controlling insect pests. As the means for controlling insect pests, control methods called mass trapping, lure-and-kill or attract-and-kill, lure-and-infect or attract-and-infect, and mating disruption are widely used in practice. To utilize the sex pheromones, economical production of a required amount of pheromone compounds is required for basic research and also for application.

*Dysmicoccus neobrevipes* (generic name: grape pineapple mealybug, and hereinafter abbreviated as "GPMB") is widely distributed in the tropical and subtropical zones, damages various crops, and thus is an economically critical insect pest. The distribution region of GPMB has been expanded, and it becomes also important to ascertain the geographical spread. Tabata et al. have identified a sex pheromone of GPMB as (+)-(E)-2-isopropyl-5-methyl-3,5-hexadienyl acetate. Tabata et al. have further revealed that, as compared with the (±)-(E)-compound: (±)-(E)-2-isopropyl-5-methyl-3,5-hexadienyl, (±)-(Z)-2-isopropyl-5-methyl-3,5-hexadienyl acetate, which is the (±)-(Z)-compound of a corresponding geometric isomer, has lower attraction activity in attraction tests using synthetic compounds. They have also reported, by using the samples obtained through optical resolution of (±)-(E)-2-isopropyl-5-methyl-3,5-hexadienyl acetate obtained by separation of geometric isomers, that a (+)-(E)-isomer showed substantially the same attraction activity as the natural pheromone; while a (−)-(E)-isomer: (−)-(E)-2-isopropyl-5-methyl-3,5-hexadienyl acetate, which is the corresponding optical isomer (i.e. an antipode), showed about a half attraction activity of that of (+)-(E)-isomer (J. Tabata et al., J. Chem. Ecol., 41, 194 (2015)).

There is a demand for a selective production method of the sex pheromone compound of GPMB for basic biological studies and agronomic studies of the compound. There is also a strong demand for an efficient production method capable of supplying a sufficient amount of the pheromone compound for the purpose of applied and practical use.

As an example of the synthesis of the sex pheromone of GPMB, J. Tabata et al. report a four-step synthesis in J. Chem. Ecol., 41, 194 (2015) in which diethyl isopropylmalonate is used as a starting material and the final step involves Wittig reaction with an ylide reagent produced from 2-formyl-3-methylbutyl acetate and 2-methylpropenyltriphenylphosphonium bromide.

In addition, A. Kaufmann et al. report, in Helv. Chim. Acta, 29, 1133 (1946), syntheses of 2-isopropyl-5-methyl-3,5-hexadienol as the syntheses of isomers of lavandulol, which is a perfume by H. L. Simon et al.

SUMMARY OF THE INVENTION

The synthesis reported by J. Tabata et al. in J. Chem. Ecol., 41, 194 (2015) is a short-step synthesis, but the product of the Wittig reaction in the final step is a mixture of (E)-2-isopropyl-5-methyl-3,5-hexadienyl acetate as a target compound and a corresponding (Z)-isomer at a ratio of 9:1. The isolation of these isomers is carried out through high performance liquid chromatography with a column of silica gel coated with silver nitrate, which is difficult to be used in industrial scale. Thus, a large scale synthesis of the target (E)-isomer involves many difficulties. The synthesis reported by A. Kaufmann et al. includes analysis techniques and structure determination techniques at that time, and thus the position and geometry of double-bonds of the synthesized compounds are unclear in many aspects.

The present invention has been completed in view of the above circumstances. According to the present invention, there is provided a geometrically selective production method of a (±)-compound of (E)-2-isopropyl-5-methyl-3,5-hexadienyl acetate as the sex pheromone of GPMB in a sufficient amount for biological studies, agronomic studies, actual application and utilization, and the like in consideration of attraction activities of geometric isomers and optical isomers. There are also provided an (E)-2-isopropyl-5-methyl-3,5-hexadienoate compound useful as a synthetic intermediate of the GPMB pheromone and a method for producing the hexadienoate compound. There is further provided a method for producing (E)-2-isopropyl-5-methyl-3,5-hexadienol, which is an isomer of lavandulol and is useful as a perfume and the like.

As a result of intensive studies, the present inventors have found that an (E)-2-isopropyl-5-methyl-3,5-hexadienoate compound can be synthesized at high selectivity. The present inventors have also found that, using the hexadienoate compound as an intermediate, (E)-2-isopropyl-5-methyl-3,5-hexadienol and an (E)-2-isopropyl-5-methyl-3,5-hexadienyl carboxylate compound can be selectively and efficiently synthesized, and have completed the present invention.

In an embodiment of the present invention, there is provided an (E)-2-isopropyl-5-methyl-3,5-hexadienoate compound represented by General Formula (2).

In another embodiment of the present invention, there is provided a method for producing an (E)-2-isopropyl-5-methyl-3,5-hexadienoate compound, the method comprising a step of dehydrating a 3-hydroxy-2-isopropyl-5-methyl-4-hexenoate compound represented by General Formula (1) to obtain the (E)-2-isopropyl-5-methyl-3,5-hexadienoate compound represented by General Formula (2).

In an embodiment of the present invention, there is provided a method for producing (E)-2-isopropyl-5-methyl-3,5-hexadienol, the method comprising a step of reducing an alkoxycarbonyl group of an (E)-2-isopropyl-5-methyl-3,5-hexadienoate compound represented by General Formula (2) to obtain the (E)-2-isopropyl-5-methyl-3,5-hexadienol represented by Formula (3).

In an embodiment of the present invention, there is provided a method for producing an (E)-2-isopropyl-5-methyl-3,5-hexadienyl carboxylate compound, the method comprising the steps of: reducing an alkoxycarbonyl group of an (E)-2-isopropyl-5-methyl-3,5-hexadienoate compound represented by General Formula (2) to obtain (E)-2-isopropyl-5-methyl-3,5-hexadienol represented by Formula (3), and esterifying the (E)-2-isopropyl-5-methyl-3,5-hexadienol (3) to obtain the (E)-2-isopropyl-5-methyl-3,5-hexadienyl carboxylate compound represented by General Formula (4).

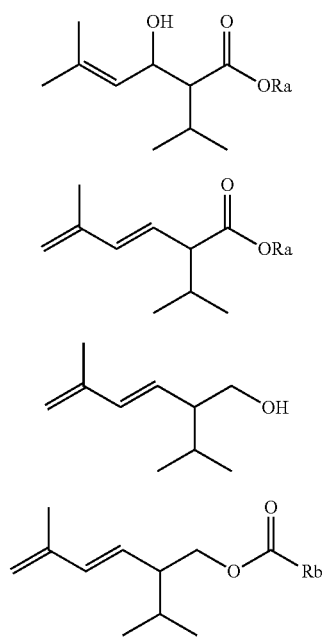

In the formulae, Ra represents a monovalent hydrocarbon group having 1 to 15 carbon atoms, and Rb represents a monovalent hydrocarbon group having 1 to 15 carbon atoms.

According to the present invention, a 3-hydroxy-2-isopropyl-5-methyl-4-hexenoate compound (1) can be used as a raw material to produce an (E)-2-isopropyl-5-methyl-3,5-hexadienoate compound (2) useful as an intermediate at high selectivity. In addition, the (E)-2-isopropyl-5-methyl-3,5-hexadienoate compound (2) can be used to selectively and efficiently synthesize (E)-2-isopropyl-5-methyl-3,5-hexadienol (3) and an (E)-2-isopropyl-5-methyl-3,5-hexadienyl carboxylate compound (4).

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

The chemical formulae of intermediates, reagents, and target compounds in the present specification can include isomers that differ in substitution sites and stereoisomers such as enantiomers and diastereomers in terms of structure. Unless otherwise stated, each chemical formula represents all the isomers in each case. An isomer may be used singly or as a mixture of two or more thereof.

In the synthesis of an (E)-2-isopropyl-5-methyl-3,5-hexadienyl carboxylate compound (4) such as (E)-2-isopropyl-5-methyl-3,5-hexadienyl acetate, which is a pheromone of GPMB, the present inventors considered an (E)-2-isopropyl-5-methyl-3,5-hexadienoate compound (2) as an intermediate. This compound can be reduced to be (E)-2-isopropyl-5-methyl-3,5-hexadienol (3), which attracts interest as a perfume, and which can be further esterified to be an (E)-2-isopropyl-5-methyl-3,5-hexadienyl carboxylate compound (4). The intermediate (E)-2-isopropyl-5-methyl-3,5-hexadienoate compound (2) is one of the dehydration products of a 3-hydroxy-2-isopropyl-5-methyl-4-hexenoate compound (1), which can be prepared by a known method. When the 3-hydroxy-2-isopropyl-5-methyl-4-hexenoate compound (1) is dehydrated, the hydrogen atom eliminated together with the hydroxy group can be a hydrogen atom Ha at the 2-position (1,2-elimination reaction) or one of six hydrogen atoms Hb including hydrogen atoms at the 6-position and 5-position (1,4-elimination reaction). Since the product can includes geometric isomers in terms of double bond, it is predicted that the dehydration reaction can produce the four products below when neither skeletal rearrangement nor positional rearrangement of double bonds are involved. In the reaction scheme below, the products surrounded by the dotted lines are products through elimination of Ha, while the other products surrounded by the solid lines are products through elimination of Hb. In the reaction scheme below, Ra represents a monovalent hydrocarbon group having 1 to 15 carbon atoms.

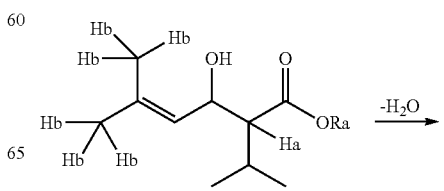

-continued

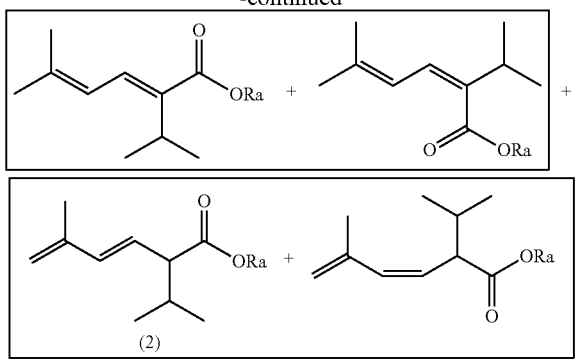

(2)

The present inventors have studied with great interest the ratio of these isomers as products of the dehydration reaction of a 3-hydroxy-2-isopropyl-5-methyl-4-hexenoate compound in various conditions. As a result, the inventors have surprisingly found that the 1,4-elimination reaction with elimination of Hb preferentially proceeds in various dehydration conditions and moreover the (E)-2-isopropyl-5-methyl-3,5-hexadienoate compound (2) having an E-double bond is produced at high selectivity as the product.

Embodiments of the present invention will now be described in detail, but it should not be construed that the present invention is limited to or by them.

According to the invention, a 3-hydroxy-2-isopropyl-5-methyl-4-hexenoate compound as the starting material is represented by General Formula (1).

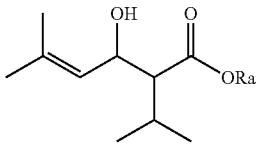

(1)

Ra represents a monovalent hydrocarbon group having 1 to 15 carbon atoms, preferably 1 to 10 carbon atoms. The monovalent hydrocarbon group may be any group that does not interfere with the subsequent steps and include a linear, branched or cyclic monovalent hydrocarbon group having an optional unsaturated bond. Preferred examples of the monovalent hydrocarbon group include linear monovalent hydrocarbon groups such as a methyl group, an ethyl group, an n-propyl group, an n-butyl group, an n-pentyl group, an n-hexyl group, an n-heptyl group, an n-octyl group, an n-nonyl group, an n-decyl group, a vinyl group, a 1-propenyl group, an allyl group, a 1-butenyl group, a 2-butenyl group, a 3-butenyl group, a 1-pentenyl group, a 2-pentenyl group, a 5-hexenyl group, a 1-heptenyl group, a 9-decenyl group, a 1,3-butadienyl group, a 1,3-pentadienyl group, a 1,5-hexadienyl group and an ethynyl group; branched monovalent hydrocarbon groups such as an isopropyl group, a 2-ethylpropyl group, a t-butyl group, a sec-butyl group, an isobutyl group, a t-amyl group, a neopentyl group, a 1-methylbutyl group, a 1-propylbutyl group, a 2-methylbutyl group, a 3-methylbutyl group, a 1-methylpentyl group, a 1-ethylpentyl group, an isopropenyl group, a 1-methyl-1-propenyl group, a 2-methyl-1-propenyl group, a 2-methyl-2-propenyl group, a 1-methyl-1-butenyl group, a 1,1-dimethyl-3-butenyl group, a 1-ethyl-1-pentenyl group, a 2,6-dimethyl-5-heptenyl group, a 2,6-dimethyl-1,5-heptadienyl group, a 2,6-dimethyl-1,6-heptadienyl group, a 6-methyl-2-methylene-5-heptenyl group, a 6-methyl-2-methylene-6-heptenyl group, a 4-methyl-1-pentenyl-3-pentenyl group and a 1-isopropylidene-4-methyl-3-pentenyl group; and cyclic monovalent hydrocarbon groups such as a cyclopropyl group, a 2-methylcyclopropyl group, a 2,2,3,3-tetramethylcyclopropyl group, a cyclobutyl group, a cyclopentyl group, a cyclopentylmethyl group, a 2-cyclopentylethyl group, a cyclohexyl group, a cyclohexylmethyl group, a dicyclohexylmethyl group, a 2-cyclohexylethyl group, a 3-cyclohexylpropyl group, a 4-cyclohexylbutyl group, a 1-methylcyclohexyl group, a 2-methylcyclohexyl group, a 3-methylcyclohexyl group, a 4-methylcyclohexyl group, a cycloheptyl group, a norbornyl group, a norbornylmethyl group, an isobornyl group, a menthyl group, a fenchyl group, an adamantyl group, a 1-cyclopentenyl group, a 2-cyclopentenyl group, a 1-cyclohexenyl group, a 1-methyl-2-cyclohexenyl group, a 2-methyl-2,5-dicyclohexadienyl group, a phenyl group, a benzyl group, a 1-phenylcyclopropyl group, a 2-phenylcyclopropyl group, a 1-phenylcyclopentyl group, a 1-phenylethyl group, a 2-phenylethyl group, a 1-methyl-2-phenylethyl group, a 1-phenylpropyl group, a 2-phenylpropyl group, a 3-phenylpropyl group, a 4-phenylbutyl group, a 1,2,3,4-tetrahydro-2-naphthyl group, a 2-phenylethenyl group, a 3-phenyl-2-propenyl group, a 1-methyl-3-phenylethenyl group, a p-tolyl group, a m-tolyl group, an o-tolyl group, a 4-ethylphenyl group, a 4-propylphenyl group, a 4-isopropylphenyl group, a 4-butylphenyl group, a 4-t-butylphenyl group, a 1-naphthyl group and a 2-naphthyl group. The monovalent hydrocarbon group can be selected appropriately in consideration of, for example, control of the boiling point and the polarity of a target compound when purification is required. Of these monovalent hydrocarbon groups, a methyl group, an ethyl group, an n-propyl group, an n-butyl group, an isopropyl group, an isobutyl group, a 2-ethylpropyl group, a t-butyl group and a benzyl group are specifically preferred from the viewpoint of easy availability of a raw material and atom economy because the monovalent hydrocarbon group is removed by reduction reaction to produce (E)-2-isopropyl-5-methyl-3,5-hexadienol (3) and is not contained by the final target product: an (E)-2-isopropyl-5-methyl-3,5-hexadienyl carboxylate compound (4).

Examples of the method for synthesizing the 3-hydroxy-2-isopropyl-5-methyl-4-hexenoate compound (1) include a method of reducing the carbonyl group at the 3-position of a 2-isopropyl-3-keto-5-methyl-4-hexenoate compound into a hydroxy group; and a method of subjecting 3-methyl-2-butenal to an aldol reaction with an enolate compound prepared from an isovalerate compound or with an equivalent of the enolate compound, such as a silylketene acetal compound.

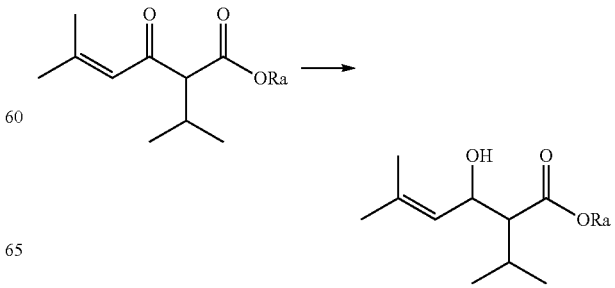

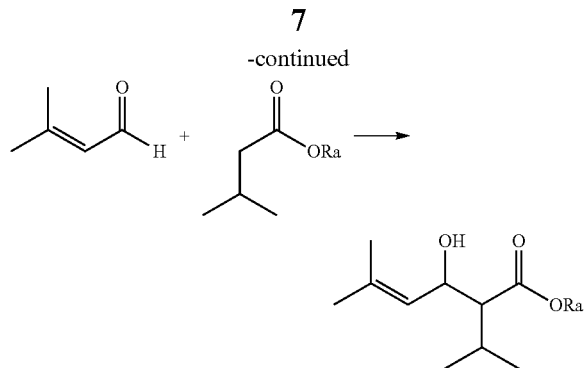

The 3-hydroxy-2-isopropyl-5-methyl-4-hexenoate compound (1) has two asymmetric carbon atoms and thus includes diastereomers. Whether a syn-isomer (1) or an anti-isomer (1) represented by the general formulae below is used, the same target (E)-2-isopropyl-5-methyl-3,5-hexadienoate compound can be produced as described later, so that the stereoselectivity is not required to be considered. In other words, the synthesis may be carried out in a condition to selectively produce one compound or in a condition to produce a mixture at any ratio.

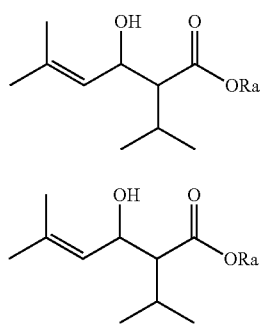

syn-(1)

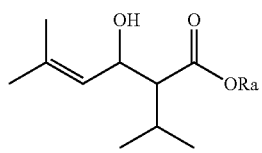

anti-(1)

The synthesis of an (E)-2-isopropyl-5-methyl-3,5-hexadienoate compound (2) by dehydration reaction of the 3-hydroxy-2-isopropyl-5-methyl-4-hexenoate compound (1) will be described.

The dehydration reaction can be carried out in various conditions, but basically comprises the steps of: converting the compound (1) having a hydroxy group into an intermediate (1x) having a leaving group X, and subsequently eliminating HX from the intermediate (1x).

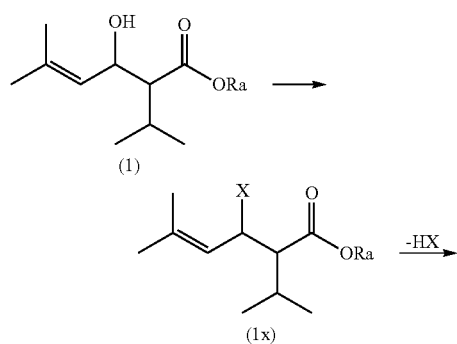

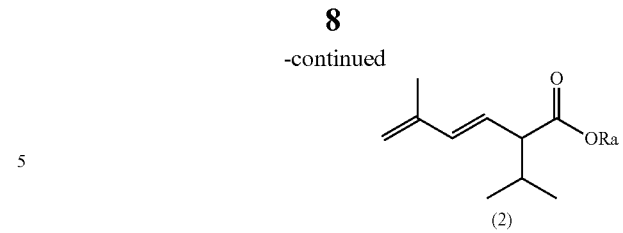

(2)

In the formulae, Ra represents the same as the above.

The intermediate (1x) may be an unstable intermediate in a reaction transition state or may be a stable compound that can be isolated. In the latter case, the intermediate (1x) may be directly subjected to elimination without isolation, or may be isolated and then subjected to elimination as the stepwise dehydration. The intermediate (1x) may also be an intermediate (1xr) below produced by migration of the positions of the double bond and the substituent X through allylic rearrangement.

(1xr)

The dehydration reaction of the compound (1) is exemplified by (i): dehydration reaction in the presence of an acid and (ii): dehydration reaction in the presence of a dehydrating agent.

In (i): the dehydration reaction in the presence of an acid, the substituent X in the intermediate (1x) is a hydroxy group activated by a protonic acid or a Lewis acid. For example, when the acid is a protonic acid, the substituent X is a protonated hydroxy group, or $H_2O^+$. In the dehydration reaction in the presence of an acid, the intermediate (1x) is generally not isolated, and the (E)-2-isopropyl-5-methyl-3,5-hexadienoate compound (2) is directly produced.

Examples of the acid used in (i): the dehydration reaction in the presence of an acid include inorganic acids or salts thereof such as hydrochloric acid, hydrobromic acid, hydroiodic acid, sulfuric acid, nitric acid, boric acid, phosphoric acid and salts thereof such as potassium hydrogen sulfate; organic acids or salts thereof such as formic acid, acetic acid, propionic acid, oxalic acid, trifluoroacetic acid, methanesulfonic acid, benzenesulfonic acid, p-toluenesulfonic acid, naphthalenesulfonic acid and salts thereof; Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide; and oxides such as alumina, silica gel and titania. The acid may be used singly or as a mixture of two or more thereof.

The amount of the acid to be used in (i): the dehydration reaction in the presence of an acid is preferably a small amount from the viewpoint of economic efficiency and may be any amount capable of achieving a practically sufficient reaction rate. The amount of the acid is preferably 0.0001 mol to 10,000 mol, more preferably 0.001 mol to 1,000 mol, still more preferably 0.001 mol to 100 mol relative to 1 mol of the compound (1) as the substrate.

In (ii): the dehydration reaction in the presence of a dehydrating agent, the dehydrating agent to be used can be selected from various known reagents commonly used as the dehydrating agent. As mentioned above, the intermediate (1x) may be directly subjected to elimination without isolation, or the intermediate (1x) may be isolated and then subjected to elimination in a stepwise manner. The substituent X in the intermediate (1x) is exemplified by X capable for forming an acidic compound HX. Specific examples of the substituent X preferably include halogen atoms capable for forming hydrohalic acids as HX such as hydrofluoric acid, hydrochloric acid, hydrobromic acid and hydroiodic acid; acyloxy groups capable for forming carboxylic acids as HX; substituted or unsubstituted phenoxy groups capable for forming phenols as HX; sulfonyloxy groups capable for forming sulfonic acids as HX including substituted sulfonic acids such as alkanesulfonic acids, arenesulfonic acids, halosulfonic acids and alkoxysulfonic acids; sulfinyloxy groups capable for forming sulfinic acids as HX including substituted sulfinic acids such as alkanesulfinic acids, arenesulfinic acids, halosulfinic acids and alkoxysulfinic acids; phosphoryloxy groups capable for forming phosphoric acids as HX including substituted and unsubstituted phosphoric acids; and phosphiryloxy groups capable for forming phosphorous acids as HX including substituted and unsubstituted phosphorous acids.

Preferred examples of the dehydrating agent which provides an intermediate (1x) having a halogen atom as X, include thionyl halides wherein the halide means fluoride, chloride, bromide or iodide (the same applies hereinafter with respect to the halide); methoxysulfonyl halides; phosphorous halides such as phosphorus tribromide; phosphorous oxyhalides such as phosphorus oxychloride; alkanesulfonyl halides such as methanesulfonyl halides and trifluoromethanesulfonyl halides; arenesulfonyl halides such as benzenesulfonyl halides, toluenesulfonyl halides, and naphthalenesulfonyl halides; and halogens such as iodine. Preferred examples of the dehydrating agent which provides an intermediate (1x) having an acyloxy group as X include acyl halides such as acetyl halides and benzoyl halides; and carboxylic acid anhydrides such as acetic anhydride and phthalic anhydride. Preferred examples of the dehydrating agent which provides an intermediate (1x) having a substituted or unsubstituted sulfonyloxy group or sulfinyloxy group as X include thionyl halides; methoxysulfonyl halides; alkanesulfonyl halides such as methanesulfonyl halides and trifluoromethanesulfonyl halides; arenesulfonyl halides such as benzenesulfonyl halides, toluenesulfonyl halides and naphthalenesulfonyl halides; alkanesulfonic acid anhydrides such as methanesulfonic anhydride and trifluoromethanesulfonic anhydride; and arenesulfonic acid anhydrides such as benzenesulfonic anhydride and p-toluenesulfonic anhydride. Preferred examples of the dehydrating agent which provides an intermediate (1x) having a substituted or unsubstituted phosphoryloxy group or phosphiryloxy group as X include phosphorous halides such as phosphorus tribromide; phosphorous oxyhalides such as phosphorus oxychloride; phosphorous oxides such as phosphorous pentoxide; methyltriphenoxyphosphonium halides; and anhydrides of inorganic phosphoric acids or phosphorous acids such as diphosphorus pentoxide and polyphosphoric acid. Examples of the other dehydrating agent include aryl isocyanates such as phenyl isocyanate; N-haloamides such as N-bromoacetamide; N-haloimides such as N-bromosuccinimide; ion exchange resins such as Amberlite IRC-50; substituted carbodiimides such as dicyclohexylcarbodiimide; inorganic salts such as potassium hydrogen sulfate, potassium hydroxide, copper sulfate, sodium acetate and florisil; dimethyl sulfoxide; and hexamethylphosphoric triamide.

The amount of the dehydrating agent to be used in (ii): the dehydration reaction in the presence of a dehydrating agent is variable depending on the type of a substrate or a dehydrating agent. The amount of the dehydrating agent is preferably 0.0001 mol to 10,000 mol, more preferably 0.001 mol to 1,000 mol, still more preferably 0.001 mol to 100 mol relative to 1 mol of the compound (1) as the substrate.

Some examples of the dehydrating agent are described twice or more in the above because they may provide a plurality of intermediates (1x) having different leaving groups X in which the respective boundaries therebetween are not necessarily clear and the difference is not important. For example, when the dehydrating agent is acetic anhydride, the compound corresponding the intermediate (1x) is an intermediate (1xa) in which the hydroxy group is acetylated. Accordingly, the leaving group X is an acetyloxy group, and acetic acid corresponding to HX will be eliminated. In another example, when the dehydrating agent is thionyl chloride, the compound corresponding the intermediate (1x) may be any of a chlorosulfinic acid ester (1xb), a sulfurous acid ester (1xc) and a chloride (1xd). These intermediates (1xb) to (1xd) can be reacted thermally or in a basic condition to undergo elimination reaction of HX, so that the dehydration reaction can proceed in the overall reaction to finally produce the target compound (2). Hence, the actual reaction intermediate may be any of the intermediates (1xb) to (1xd), or may be any intermediate produced from the intermediates (1xa) to (1xd) by migration of the positions of the double bond and the substituent X through the corresponding allylic rearrangement as mentioned above. The structure of the actual intermediate is not important, and the intermediate may have any structure that finally produces the target compound (2). The dehydrating agent may be used as a reaction reagent in the first step, in which the compound (1) is converted to the intermediate (1x), in the stepwise dehydration reaction.

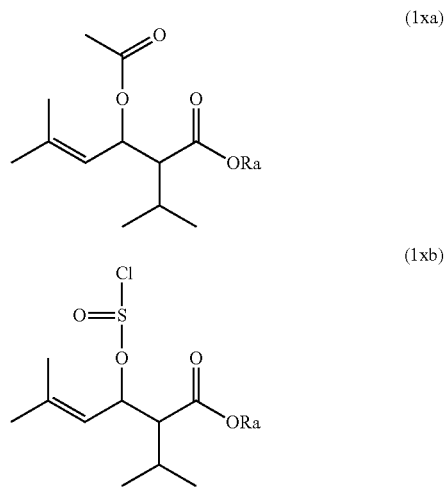

11

-continued

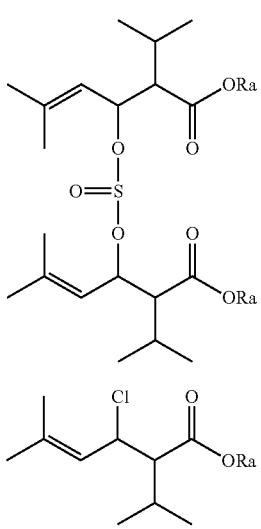

(1xc)

(1xd)

In (ii): the dehydration reaction in the presence of a dehydrating agent, the dehydrating agent may be used in combination with a base. Examples of the base include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide and potassium t-amyloxide; hydroxide salts such as sodium hydroxide, lithium hydroxide, potassium hydroxide and barium hydroxide; carbonates such as lithium carbonate, sodium carbonate, potassium carbonate, calcium carbonate, sodium hydrogen carbonate and potassium hydrogen carbonate wherein such a carbonate may be combined, for example, with a halide salt or a perchlorate salt; organometallic reagents such as methyllithium, ethyllithium, n-butyllithium, methylmagnesium chloride and dimsyl sodium; metal amides such as sodium amide, lithium amide, lithium diisopropylamide, lithium hexamethyldisilazide, sodium hexamethyldisilazide and lithium dicyclohexylamide; metal hydrides such as sodium hydride, potassium hydride and calcium hydride; organic bases such as triethylamine, diisopropylethylamine, tributylamine, N,N-dimethylaniline, N,N-diethylaniline, pyridine, 4-dimethylaminopyridine, quinoline, pyrrolidine, piperidine, collidine, lutidine, morpholine, piperazine, 1,5-diazabicyclo[4.3.0]non-5-ene (DBN), 1,8-diazabicyclo[5.4.0]undec-7-ene (DBU), 1,4-diazabicyclo[2.2.2]octane and trimethyl phosphite; and quaternary onium salts such as tetraethylammonium chloride, tetrabutylammonium bromide and tetrabutylphosphonium bromide. The base may be used singly or as a mixture of two or more thereof, and can be selected in consideration of the type, reactivity and selectivity of a substrate.

The amount of the base to be used in (ii): the dehydration reaction in the presence of a dehydrating agent is variable depending on the type of a substrate or a base. The amount of the base is preferably 0.0001 mol to 10,000 mol, more preferably 0.001 mol to 1,000 mol, still more preferably 0.001 mol to 100 mol relative to 1 mol of the compound (1) as the substrate.

Depending on the type of a base or reaction conditions, slight retro-aldol reaction as a side reaction may proceed competitively, so that the base and the reaction conditions are selected appropriately so as to suppress the side reaction and to increase an intended reaction rate. When an alkoxide is selected as the base, a substrate having an alkoxide containing $RaO^-$ corresponding to the substituent $CO_2Ra$ is preferably used because the complication of a reaction system through transesterification can be prevented. Such a base is preferably used as a reaction reagent in the second step, in which the intermediate (1x) is converted to the compound (2) in the stepwise dehydration reaction.

The dehydration reaction of the compound (1) can be carried out in the absence or presence of a solvent at room temperature, while optionally cooling or heating the reaction mixture.

Examples of the solvent to be used in the dehydration reaction include water; liquid ammonia; alcohols such as methanol and ethanol; ethers such as diethyl ether, di-n-butyl ether, tetrahydrofuran and 1,4-dioxane; hydrocarbons such as hexane, heptane, benzene, toluene, xylene and cumene; ketones such as acetone and 2-butanone; esters such as ethyl formate, methyl acetate, ethyl acetate, butyl acetate and n-amyl acetate; aprotic polar solvents such as N,N-dimethylformamide, 1,3-dimethyl-2-imidazolidinone, dimethyl sulfoxide and hexamethylphosphoric triamide; nitriles such as acetonitrile and propionitrile; and amines such as pyridine, ethylamine, diethylamine, triethylamine, aniline and dimethylaniline. The solvent can be used singly or as a mixture of two or more thereof.

The amount of the solvent to be used in the dehydration reaction is preferably 0.01 parts to 100,000 parts, more preferably 0.1 parts to 10,000 parts, still more preferably 1 part to 1,000 parts relative to 100 parts of the substrate. When an alcohol is selected as the solvent, an alcohol RaOH corresponding to the substituent $CO_2Ra$ in the substrate or a tertiary alcohol having low nucleophilicity is preferably used because the complication of a reaction system through transesterification can be prevented.

The reaction temperature and reaction time for the dehydration reaction of the compound (1) can be appropriately selected. It is preferable to allow the reaction to proceed sufficiently by monitoring the progress of the reaction with gas chromatography (GC) or thin-layer chromatography (TLC). The reaction temperature is preferably from 0° C. to the boiling point of the solvent, more preferably 10° C. to 100° C. The reaction time is typically from 5 minutes to 240 hours. The second step of the stepwise dehydration reaction can be allowed to proceed only by heating the intermediate (1x) in the presence or absence of a solvent depending on the type of the intermediate (1x). It is also preferable to remove generated water from the system as an azeotrope with a solvent for acceleration of the reaction.

It has been found that, in the synthesis of (E)-2-isopropyl-5-methyl-3,5-hexadienoate compound (2) by dehydration reaction of 3-hydroxy-2-isopropyl-5-methyl-4-hexenoate compound (1), the compound (2) can be obtained with sufficient selectivity and yield for industrial scale by selecting appropriate conditions from the above dehydration reaction conditions. In the synthesis, it is noteworthy that almost no 2-isopropyl-5-methyl-2,4-hexadienolate, which is an α,β-unsaturated ester supposed to be relatively stable, is formed as the product, and almost no (Z)-2-isopropyl-5-methyl-3,5-hexadienoate compound, which is a geometric isomer of the compound (2), is formed. In addition, each of a syn-isomer and an anti-isomer that are stereoisomers of the compound (1) provides the same target compound. In other words, the reaction is stereochemically convergent and is not stereospecific. Accordingly, the stereoisomers of the compound (1) are not required to be separately produced. Such a method thus has a high industrial value. The high selectivity with respect to these points can be considered to be because, for example, an isopropyl group at the 2-position is bulky, the geometry of the double bond at the 3-position with respect to carbocation considered to be in the reaction transition state is E, and a carbocation intermediate having cation at the 5-position is stable. The presence of the carbocation at the 5-position with the E geometry of the double bond at the 3-position is considered to be supported by a case in which an (E)-5-hydroxy-2-isopropyl-3-hexenoate compound having hydration at the 5-position can be isolated, as shown in Example. The resulting (E)-5-hydroxy-2-isopropyl-3-hexenoate compound can also be used as the substrate for the dehydration reaction in the same manner as the 3-hydroxy-2-isopropyl-5-methyl-4-hexenoate compound (1).

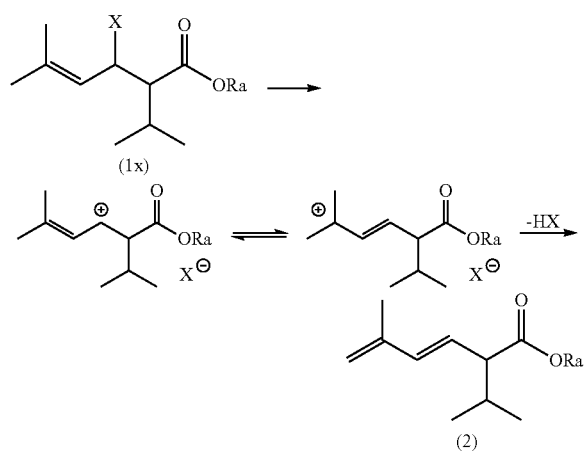

When a 3-hydroxy-2-isopropyl-5-methyl-4-hexenoate compound (1) is dehydrated in the same dehydration reaction conditions as those by Inoue et al. in which a 2-methyl-5-methyl-2,4-hexadienolate compound is obtained from a 3-hydroxy-2,5-dimethyl-4-hexenoate compound having a bulky isopropyl group at the 2-position of the 3-hydroxy-2-isopropyl-5-methyl-4-hexenoate compound (1) replaced by a methyl group, an (E)-2-isopropyl-5-methyl-3,5-hexadienoate compound (2) is obtained. This study will be specifically described in Example 7, and suggests that the structure at the 2-position of a substrate greatly affects the selectivity of the dehydration reaction.

A crude product of the target (E)-2-isopropyl-5-methyl-3,5-hexadienoate compound (2) obtained by the above dehydration reaction may be directly subjected to the subsequent step if it has sufficient purity. It may be purified by a method appropriately selected from purification methods commonly used in organic synthesis, such as distillation, various types of chromatography and recrystallization.

Next, the synthesis of (E)-2-isopropyl-5-methyl-3,5-hexadienol (3) by reduction of the produced (E)-2-isopropyl-5-methyl-3,5-hexadienoate compound (2) will be described.

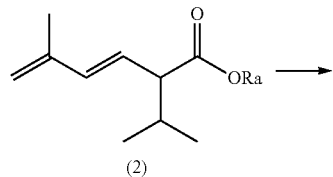

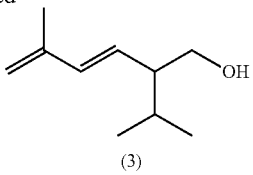

The (E)-2-isopropyl-5-methyl-3,5-hexadienoate compound (2) can be directly subjected to the reduction described later to produce (E)-2-isopropyl-5-methyl-3,5-hexadienol (3). Alternatively, the compound (2) can be converted into (E)-2-isopropyl-5-methyl-3,5-hexadienoic acid, and then the acid can be subjected to reduction. First, the conversion of the (E)-2-isopropyl-5-methyl-3,5-hexadienoate compound (2) into (E)-2-isopropyl-5-methyl-3,5-hexadienoic acid will be described.

The conversion of the (E)-2-isopropyl-5-methyl-3,5-hexadienoate compound (2) into (E)-2-isopropyl-5-methyl-3,5-hexadienoic acid can be carried out by a known conversion reaction from an ester to a carboxylic acid. The conversion reaction is exemplified by a hydrolysis reaction in a basic or neutral condition, as well as an elimination reaction in an acidic condition. The hydrolysis reaction is preferable when Ra of the ester as the substrate is a primary or secondary hydrocarbon group, while the elimination reaction in an acidic condition is preferable when Ra is a tertiary hydrocarbon group. The hydrolysis reaction is typically carried out in a solvent in the presence of a base or a salt, and water contained by the solvent is reacted, or water is subsequently added and reacted. The elimination reaction is typically carried out in a solvent in the presence of an acid. In either reaction, the reaction may be carried out while optionally cooling or heating the reaction mixture.

Examples of the base to be used in the hydrolysis reaction include hydroxide salts such as sodium hydroxide, lithium hydroxide, potassium hydroxide and barium hydroxide, preferably a metal hydroxide, more preferably an alkali metal hydroxide or an alkaline earth metal hydroxide; carbonates such as sodium carbonate, potassium carbonate, sodium hydrogen carbonate and potassium hydrogen carbonate, preferably an alkali metal carbonate or an alkali metal bicarbonate; and alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide and potassium t-amyloxide, preferably a metal alkoxide, more preferably an alkali metal alkoxide.

Examples of the salts to be used in the hydrolysis include halides such as lithium iodide, lithium bromide, trimethylsilyl iodide and trimethylsilyl bromide, preferably an alkali metal halide.

Examples of the acid to be used in the elimination reaction include inorganic acids or salts thereof such as hydrochloric acid, hydrobromic acid, hydroiodic acid, sulfuric acid, nitric acid, boric acid and phosphoric acid or salts thereof such as potassium hydrogen sulfate; organic acids or salts thereof such as formic acid, acetic acid, propionic acid, oxalic acid, trifluoroacetic acid, methanesulfonic acid, benzenesulfonic acid, p-toluenesulfonic acid and naphthalenesulfonic acid or salts thereof; Lewis acids such as aluminum trichloride, aluminum ethoxide, aluminum isopropoxide, aluminum oxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium (IV) oxide; and oxides such as alumina, silica gel and titania. The acid may be used singly or as a mixture of two or more thereof.

Examples of the solvent to be used in the hydrolysis reaction or the elimination reaction include water; alcohols such as methanol, ethanol, isopropyl alcohol, t-butyl alcohol, benzyl alcohol, methoxyethanol, ethoxyethanol, diethylene glycol monomethyl ether and triethylene glycol monomethyl ether; ethers such as diethyl ether, di-n-butyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethyl sulfoxide (DMSO) and hexamethylphosphoric triamide (HMPA); and nitriles such as acetonitrile and propionitrile. The solvent can be used singly or as a mixture of two or more thereof.

The reaction temperature and reaction time of the hydrolysis reaction or the elimination reaction can be selected appropriately. The reaction is preferably allowed to proceed sufficiently by monitoring the progress of the reaction by gas chromatography (GC) or thin-layer chromatography (TLC). The reaction temperature is preferably from −78° C. to the boiling point of a solvent, more preferably from −10° C. to 100° C. The reaction time is typically from 5 minutes to 240 hours.

The work-up of the reaction, and the isolation and purification of the target compound can be carried out by a method appropriately selected from purification methods commonly used in organic synthesis, such as vacuum distillation and various types of chromatography. A crude product of the target compound having sufficient purity may be directly subjected to the subsequent step.

Next, the step of reducing the (E)-2-isopropyl-5-methyl-3,5-hexadienoate compound (2) or (E)-2-isopropyl-5-methyl-3,5-hexadienoic acid to obtain (E)-2-isopropyl-5-methyl-3,5-hexadienol (3) will be described.

The reduction can be carried out by a known reduction reaction from a carboxylic ester or a carboxylic acid to an alcohol. In the reduction, a reaction substrate is reacted with a reducing agent typically in a solvent while optionally cooling or heating the reaction mixture. Regarding the reaction substrate, although depending on the type of a reducing agent or reaction conditions, when Ra of the ester is a primary or secondary alkyl group, the (E)-2-isopropyl-5-methyl-3,5-hexadienoate compound (2) is preferably directly used as the reaction substrate for the reduction. When Ra of the ester is a tertiary group particularly having large steric hindrance, a side reaction such as reduction of a double bond may proceed in some cases. Such an ester is preferably converted beforehand by the above method into (E)-2-isopropyl-5-methyl-3,5-hexadienoic acid, which can be used as the substrate for the reduction.

Examples of the reducing agent in the reduction reaction include hydrogen; boron compounds such as borane, alkylboranes, dialkylboranes and bis(3-methyl-2-butyl)borane; dialkylsilanes; trialkylsilanes; alkylaluminums; dialkylaluminums; metal hydrides such as sodium hydride, lithium hydride, potassium hydride and calcium hydride; and complex hydrides and alkoxy or alkyl derivatives thereof such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-tert-butoxyaluminum hydride, sodium bis(2-methoxyethoxy)aluminum hydride, lithium triethylborohydride and diisobutylaluminum hydride and alkoxy or alkyl derivatives thereof. Specifically, the complex hydride is preferably used from the viewpoint of reaction conditions, easy work-up, easy isolation of a product and the like.

The amount of the reducing agent to be used in the reduction reaction is variable depending on a type of reducing agent, reaction conditions or the like. It is in general preferably from 0.5 mol to a large excess amount (e.g. from 2 mol to 500 mol), more preferably from 0.9 to 8.0 mol relative to 1 mol of the substrate.

Examples of the solvent to be used in the reduction preferably include water; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran and 1,4-dioxane; alcohols such as methanol, ethanol, 1-propanol, 2-propanol, ethylene glycol monomethyl ether and diethylene glycol monomethyl ether; nitriles such as acetonitrile; ketones such as acetone and 2-butanone; esters such as ethyl acetate and n-butyl acetate; and aprotic polar solvents such as N,N-dimethylformamide, dimethyl sulfoxide and hexamethylphosphoric triamide. The solvent can be used singly or as a mixture of two or more thereof.

The solvent to be used in the reduction reaction is appropriately selected depending on the type of a reducing agent to be used. As for a preferred combination of a reducing agent and a solvent, when lithium borohydride is used as the reducing agent, for example, an ether, a mixed solvent of an ether and an alcohol, or a mixed solvent of an ether and a hydrocarbon is used. When lithium aluminum hydride is used as the reducing agent, for example, an ether, or a mixed solvent of an ether and a hydrocarbon is used.

The reaction temperature or reaction time in the reduction reaction is variable depending on a reagent or a solvent. For example, when lithium aluminum hydride is used as the reducing agent in tetrahydrofuran, the reaction temperature is preferably −78° C. to 50° C., more preferably −70 to 20° C. The reaction time can be appropriately selected. The reaction is preferably allowed to be completed by monitoring the reaction by gas chromatography (GC) or silica gel thin-layer chromatography (TLC) from the viewpoint of yield. The reaction time is typically about 0.5 to 96 hours.

The isolation or purification of the (E)-2-isopropyl-5-methyl-3,5-hexadienol (3) synthesized in the above manner can be carried out by a method appropriately selected from purification methods commonly used in organic synthesis, such as distillation and various types of chromatography. It is preferably carried out by vacuum distillation from the viewpoint of industrial cost efficiency. A crude product of the compound (3) having sufficient purity can be directly subjected to the subsequent step.

Next, the synthesis of an (E)-2-isopropyl-5-methyl-3,5-hexadienyl carboxylate compound (4) by esterification of the (E)-2-isopropyl-5-methyl-3,5-hexadienol (3) will be described.

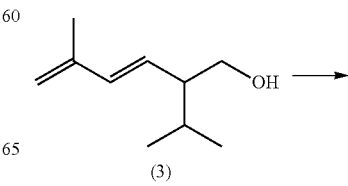

(3)

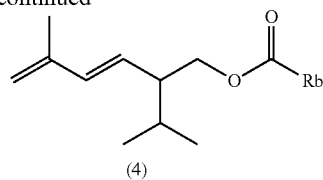

(4)

Rb represents a monovalent hydrocarbon group having 1 to 15 carbon atoms.

Rb is exemplified by the same substituents as for Ra and is particularly preferably a methyl group, an ethyl group, an n-propyl group, an isopropyl group, an isobutyl group, a sec-butyl group, a 4-methylpentyl group, a 2-methyl-1-propenyl group, or a 2-methyl-2-propenyl group.

The synthesis of an (E)-2-isopropyl-5-methyl-3,5-hexadienyl carboxylate compound (4) by esterification of (E)-2-isopropyl-5-methyl-3,5-hexadienol (3) can be carried out by a known ester production method such as a reaction with an acylating agent, a reaction with a carboxylic acid, transesterification, and a method in which the compound (3) is converted into an alkylating agent and then the alkylating agent is reacted with a carboxylic acid.

In the reaction with an acylating agent, the (E)-2-isopropyl-5-methyl-3,5-hexadienol (3) as the reaction substrate is reacted with an acylating agent and a base sequentially or concurrently, in a single solvent or a mixed solvent of two or more solvents.

Examples of the solvent to be used in the reaction with an acylating agent preferably include chlorinated solvents such as methylene chloride, chloroform and trichloroethylene; hydrocarbons such as hexane, heptane, benzene, toluene, xylene and cumene; ethers such as diethyl ether, dibutyl ether, diethylene glycol diethyl ether, diethylene glycol dimethyl ether, tetrahydrofuran and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide and hexamethylphosphoric triamide. The solvent may be used singly or as a mixture of two or more thereof.

Examples of the acylating agent preferably include carboxylic acid chlorides, carboxylic acid bromides, carboxylic acid anhydrides, carboxylic trifluoroacetic anhydrides, carboxylic methanesulfonic anhydrides, carboxylic trifluoromethanesulfonic anhydrides, carboxylic benzenesulfonic anhydrides, carboxylic p-toluenesulfonic anhydrides, and p-nitrophenyl carboxylates.

Examples of the base preferably include triethylamine, diisopropylethylamine, N,N-dimethylaniline, pyridine and 4-dimethylaminopyridine.

The reaction with an acylating agent such as an acid anhydride can also be carried out in the presence of an acid catalyst instead of the base. The acid catalyst is preferably selected from inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide.

The reaction temperature can be appropriately selected depending on the type of an acylating agent and reaction conditions. The reaction temperature is in general preferably from −50° C. to the boiling point of a solvent, more preferably from −20° C. to room temperature. The room temperature means 5° C. to 35° C. hereinafter. The amount of the acylating agent is preferably 1 to 500 mol, more preferably 1 to 50 mol, still more preferably 1 to 5 mol relative to 1 mol of the compound (3) as the raw material.

The reaction with a carboxylic acid is a dehydration reaction of (E)-2-isopropyl-5-methyl-3,5-hexadienol (3) with the carboxylic acid and is typically carried out in the presence of an acid catalyst. The amount of the carboxylic acid is preferably 1 to 500 mol, more preferably 1 to 50 mol, still more preferably 1 to 5 mol relative to 1 mol of the compound (3) as the raw material.

Examples of the acid catalyst to be used in the reaction of the compound (3) with a carboxylic acid include inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. The acid catalyst may be used singly or as a mixture of two or more thereof. The amount of the acid catalyst is preferably 0.0001 to 100 mol, more preferably 0.001 to 1 mol, still more preferably a catalytic amount of 0.01 to 0.05 mol relative to 1 mol of the compound (3) as the raw material.

Examples of the solvent to be used in the reaction of the compound (3) with a carboxylic acid include the same solvents exemplified in the reaction with the acylating agent.

The reaction temperature of the compound (3) with a carboxylic acid can be appropriately selected depending on the type of a carboxylic acid and reaction conditions. The reaction temperature is in general preferably from −50° C. to the boiling point of a solvent, more preferably from room temperature to the boiling point of a solvent. It is also preferable to use a solvent containing a hydrocarbon such as hexane, heptane, benzene, toluene, xylene and cumene and allow the reaction to proceed while removing generated water from the system as an azeotrope. In this case, water can be distilled off while refluxing the reaction mixture at the boiling point of a solvent at normal pressure. Alternatively, water can be distilled off at a temperature lower than the boiling point under reduced pressure.

The transesterification is carried out in such a manner that (E)-2-isopropyl-5-methyl-3,5-hexadienol (3) is reacted with an alkyl carboxylate in the presence of a catalyst, and the generated alcohol is removed. The alkyl carboxylate is preferably a primary alkyl ester of a carboxylic acid, particularly preferably a methyl carboxylate, an ethyl carboxylate or an n-propyl carboxylate from the viewpoint of price and easy progress of the reaction. The amount of the alkyl carboxylate is preferably 1 to 500 mol, more preferably 1 to 50 mol, still more preferably 1 to 5 mol relative to 1 mol of the compound (3) as the raw material.

Examples of the catalyst to be used in the transesterification include inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; bases such as sodium methoxide, sodium ethoxide, potassium t-butoxide and 4-dimethylaminopyridine; salts such as sodium cyanide, potassium cyanide, sodium acetate, potassium acetate, calcium acetate, tin acetate, aluminum acetate, aluminum acetoacetate and alumina; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. The catalyst may be used singly or as a mixture of two or more thereof. The amount of the catalyst is preferably 0.0001 to 100 mol, more preferably 0.001 to 1 mol, still more preferably a catalytic amount of 0.01 to 0.05 mol relative to 1 mol of the compound (3) as the raw material.

The transesterification can be carried out without a solvent. An alkyl carboxylate itself as the reaction reagent may be used also as the solvent. Such a reaction is preferable because an additional operation such as concentration and solvent recovery is not necessary. It is possible that a solvent is used supplementally. In this case, examples of the solvent include hydrocarbons such as hexane, heptane, benzene, toluene, xylene and cumene; and ethers such as diethyl ether, dibutyl ether, diethylene glycol diethyl ether, diethylene glycol dimethyl ether, tetrahydrofuran and 1,4-dioxane. The solvent may be used singly or as a mixture of two or more thereof. The reaction temperature can be appropriately selected depending on the type of an alkyl carboxylate and reaction conditions. The reaction is typically carried out with heating and is preferably carried out around the boiling point of a lower alcohol having a low boiling point generated by the transesterification reaction, such as methanol, ethanol and 1-propanol, while distilling off the generated lower alcohol, to obtain good results. The alcohol may be distilled off under reduced pressure at a temperature lower than the boiling point.

In the method in which the compound (3) is converted into an alkylating agent and the alkylating agent is reacted with a carboxylic acid, for example, (E)-2-isopropyl-5-methyl-3,5-hexadienol (3) is converted into a corresponding halide such as chloride, bromide or iodide, or a corresponding sulfonate such as methanesulfonate, trifluoromethanesulfonate, benzenesulfonate or a p-toluenesulfonate; and then reacted with a carboxylic acid typically in a solvent in a basic condition. The solvent, base, reaction time and reaction temperature are exemplified by the same solvents, bases and conditions described in the reaction of the compound (3) with the acylating agent. Instead of the combination of a carboxylic acid and a base, a carboxylate salt such as a sodium carboxylate, a lithium carboxylate, a potassium carboxylate and an ammonium carboxylate may be used.

The isolation or purification of the (E)-2-isopropyl-5-methyl-3,5-hexadienyl carboxylate compound (4) synthesized as above can be carried out by a method appropriately selected from purification methods commonly used in organic synthesis, such as vacuum distillation and various types of chromatography. It is preferably carried out by vacuum distillation from the viewpoint of industrial cost efficiency.

As described above, efficient methods having short synthesizing routes for producing an (E)-2-isopropyl-5-methyl-3,5-hexadienoate compound (2), (E)-2-isopropyl-5-methyl-3,5-hexadienol (3) and an (E)-2-isopropyl-5-methyl-3,5-hexadienyl carboxylate compound (4) are provided in order to supply the compounds in sufficient amounts for application, utilization and the like.

EXAMPLES

The present invention will next be described in further detail with reference to Examples. It should not be construed that the present invention is limited to or by Examples.

The values obtained by gas chromatography (GC) analyses are used as the purities of raw materials, products and intermediates, and expressed as % GC. As for the GC conditions, a gas chromatograph of Shimazdu GC-14A with a column of 5% Ph-Me silicone having 0.25 mm $\phi \times 25$ m, a carrier gas of helium, and flame ionization detector (FID) were used.

Since a raw material and a product of the reaction do not necessarily have purity of 100%, the yield is expressed as the conversion yield below on basis of the % GC. Since the detector sensitivity of the gas chromatography is variable depending on a type of compound, particularly when a starting material or a crude product is crude, a conversion yield may be more than 100%.

$$\text{conversion yield}(\%) = \left(\frac{\text{weight of product of the reaction} \times \% \ GC}{\text{molecular weight of the product}}\right) + \left(\frac{\text{weight of starting material of the reaction} \times \% \ GC}{\text{molecular weight of the starting material}}\right) \times 100$$

The compound samples for spectrum measurement were prepared by purification of crude products as necessary.

[I] Synthesis Example of
3-Hydroxy-2-Isopropyl-5-Methyl-4-Hexenoate
compound represented by General Formula (1)

Reference Example 1

Synthesis Example of ethyl 3-hydroxy-2-isopropyl-5-methyl-4-hexenoate corresponding to General Formula (1) in which Ra is a Ethyl Group (CH$_3$CH$_2$, Et)

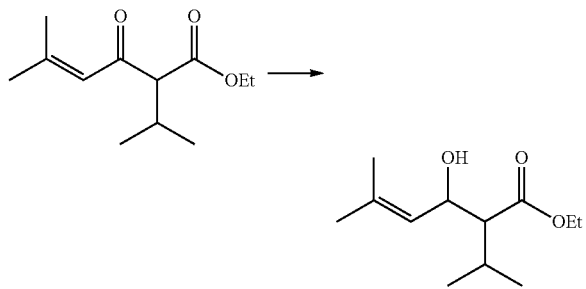

Under a nitrogen atmosphere, 292 ml of 4.4M solution of zinc tetrahydroborate in tetrahydrofuran was added to a mixture of 75 g of ethyl 2-isopropyl-3-keto-5-methyl-4-hexenoate and 800 ml of diethyl ether, while the mixture was stirred at room temperature. After the reaction mixture was stirred at room temperature for 24 hours, it was subjected to addition of a mixture of 20 g of acetic acid and 380 g of water, and then extracted with ethyl acetate. The separated organic phase was subjected to usual work-up including washing, drying and concentration to obtain 57.5 g of ethyl 3-hydroxy-2-isopropyl-5-methyl-4-hexenoate (the main product: a syn-isomer, yield 78%) as the target compound.

Ethyl anti-3-hydroxy-2-isopropyl-5-methyl-4-hexenoate

Yellowish Oil
IR (D-ATR): ν=3432 (br.), 2963, 2935, 2875, 1731, 1373, 1239, 1178, 1154, 1029 cm$^{-1}$.
$^1$H-NMR (500 MHz, CDCl$_3$): δ=0.96 (3H, d, J=6.1 Hz), 0.97 (3H, d, J=5.7 Hz), 1.23 (3H, t, J=7.3 Hz), 1.70 (31H, d, J=1.5 Hz), 1.71 (3H, d, J=1.1 Hz), 2.03 (1H, s, OH), 2.05-2.14 (2H, m), 2.41 (1H, dd, J=6.5, 7.7 Hz), 4.11 (21H, q, J=7.3 Hz), 4.59 (1H, dd, J=7.6, 9.2 Hz), 5.34 (1H, dq-like, J=9.6, 1.5 Hz) ppm.
$^{13}$C-NMR (125 MHz, CDCl$_3$): δ=14.30, 18.20, 19.28, 21.32, 25.88, 27.16, 57.92, 59.94, 67.50, 124.84, 137.02, 173.22 ppm.
GC-MS (EI, 70 eV): 29, 41, 55, 69, 85 (base peak), 101, 115, 130, 153, 171, 199, 214 (M$^+$).

Synthesis of (E)-2-Isopropyl-5-Methyl-3,5-Hexadienoate Compound represented by General Formula (2)

Example 1

Synthesis Example 1 of Ethyl (E)-2-isopropyl-5-methyl-3,5-hexadienoate Corresponding to General Formula (2) in which Ra is a Ethyl Group (CH$_3$CH$_2$, Et)

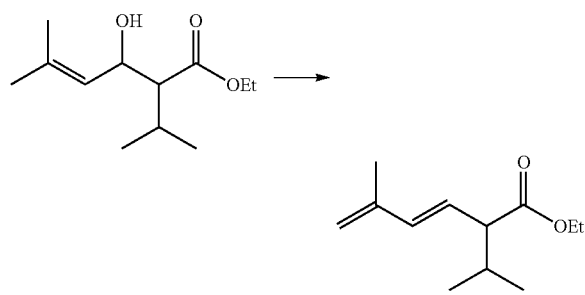

Under a nitrogen atmosphere, a mixture of 9.69 g of ethyl 3-hydroxy-2-isopropyl-5-methyl-4-hexenoate and 7.20 g of acetic anhydride was stirred at 150° C. for 3 hours. The reaction mixture was directly subjected to vacuum distillation to remove excess acetic anhydride and acetic acid generated by the reaction, and then the target compound was distilled to obtain 6.92 g of ethyl (E)-2-isopropyl-5-methyl-3,5-hexadienoate (70.4 to 93.9% GC, yield 78%) as the target compound. The geometry of the double bond of the target compound was determined by the fact that the $^1$H-$^1$H coupling constant J between the 3- and 4-positions was 15.7 Hz in $^1$H-NMR and by correlations in a 2D-NOESY spectrum, as shown below. As a result of the GC analyses of the reaction mixture and the product, ethyl (Z)-2-isopropyl-5-methyl-3,5-hexadienoate, which was a geometric isomer of the target compound, was not detected.

Ethyl (E)-2-isopropyl-5-methyl-3,5-hexadienoate

Colorless-Yellowish Oil
Boiling point: 74 to 80° C./400 Pa
IR (D-ATR): ν=2963, 2873, 1732, 1467, 1370, 1236, 1176, 1152, 1032, 969, 888 cm$^{-1}$.
$^1$H-NMR (500 MHz, CDCl$_3$): δ=0.87 (3H, d, J=6.9 Hz), 0.92 (3H, d, J=6.5 Hz), 1.25 (3H, t, J=7.3 Hz), 1.84 (3H, s), 1.95-2.06 (1H, m), 2.70 (1H, t, J=8.9 Hz), 4.08-4.18 (2H, m), 4.92 (1H, br.s), 4.93 (1H, br.s), 5.62 (1H, dd, J=9.6, 15.7 Hz), 6.17 (1H, d, J=15.7 Hz) ppm.
2D-NOESY: Correlations of nuclear Overhauser effect (NOE) are shown by the double-headed arrows in the scheme below.

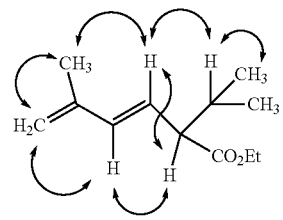

$^{13}$C-NMR (125 MHz, CDCl$_3$): δ=14.21, 18.57, 19.84, 20.70, 31.19, 57.21, 60.31, 116.10, 126.83, 135.81, 141.56, 174.02 ppm.
GC-MS (EI, 70 eV): 41, 53, 67, 81 (base peak), 91, 111, 123, 139, 154, 181, 196 (M$^+$).
GC-MS (CI, isobutane): 123, 197 [(M+H)$^+$].

Example 2

Synthesis Example 2 of Ethyl (E)-2-isopropyl-5-methyl-3,5-hexadienoate Corresponding General Formula (2) in which Ra is an Ethyl Group (CH$_3$CH$_2$, Et)

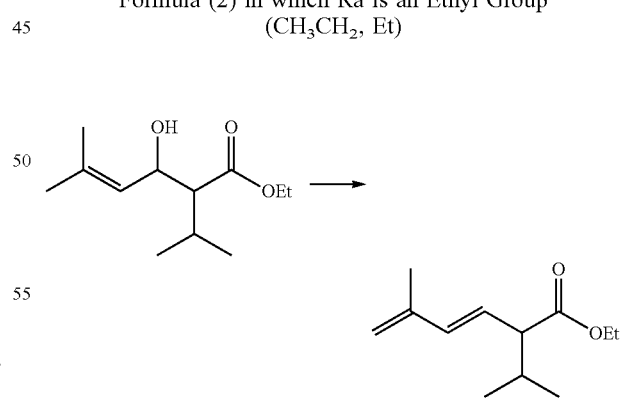

Under a nitrogen atmosphere, 26 mg of pyridine was added to a mixture of 70.2 mg of ethyl 3-hydroxy-2-isopropyl-5-methyl-4-hexenoate, 95.0 mg of methanesulfonic anhydride, 3.0 g of diethyl ether and 3.0 g of methylene chloride, while the mixture was stirred at room temperature. After the reaction mixture was stirred at room temperature for 14 hours, it was poured into a diluted hydrochloric acid and extracted with diethyl ether. The separated organic phase was subjected to usual work-up including washing, drying and concentration to obtain 57.8 mg of ethyl (E)-2-isopropyl-5-methyl-3,5-hexadienoate (95.0% GC, yield 85%) as the target compound. As a result of the GC analyses of the reaction mixture and the product, ethyl (Z)-2-isopropyl-5-methyl-3,5-hexadienoate, which was a geometric isomer of the target compound, was not detected. The product was the same as the product in Example 1.

Example 3

Synthesis Example 3 of Ethyl (E)-2-isopropyl-5-methyl-3,5-hexadienoate Corresponding General Formula 2 in which Ra is an Ethyl Group (CH$_3$CH$_2$, Et)

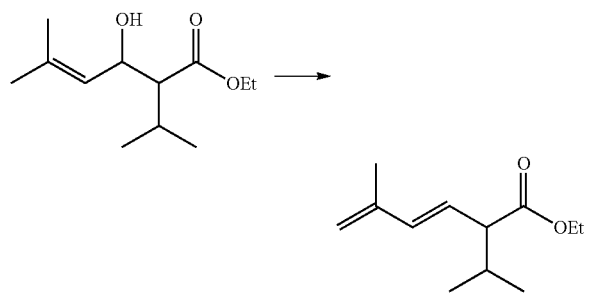

Under a nitrogen atmosphere, 600 mg of triethylamine and 535 mg of methanesulfonyl chloride were sequentially added to a mixture of 672 mg of ethyl 3-hydroxy-2-isopropyl-5-methyl-4-hexenoate and 20 ml of tetrahydrofuran, while the mixture was stirred and cooled on ice. After the reaction mixture was stirred and cooled on ice for 1 hour, it was poured into water and extracted with ethyl acetate. The separated organic phase was subjected to usual work-up including washing, drying and concentration to obtain 880 mg of ethyl (E)-2-isopropyl-5-methyl-3,5-hexadienoate (89.1% GC, yield 85%) as the target compound. As a result of the GC analyses of the reaction mixture and the product, ethyl (Z)-2-isopropyl-5-methyl-3,5-hexadienoate, which was a geometric isomer of the target compound, was not detected. The product was the same as the product in Example 1.

Example 4

Synthesis Example 4 of Ethyl (E)-2-isopropyl-5-methyl-3,5-hexadienoate Corresponding to General Formula 2 in which Ra is an Ethyl Group (CH$_3$CH$_2$, Et)

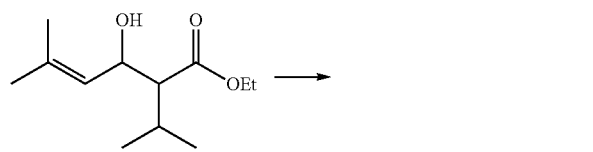

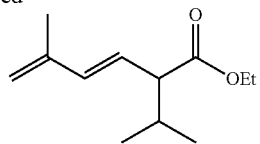

Under a nitrogen atmosphere, 100 μl of thionyl chloride was added to a mixture of 0.162 g of ethyl 3-hydroxy-2-isopropyl-5-methyl-4-hexenoate, 0.300 g of pyridine and 10 ml of methylene chloride, while the mixture was stirred at room temperature. After the reaction mixture was stirred at room temperature for 14 hours, it was poured into dilute hydrochloric acid and extracted with diethyl ether. The separated organic phase was subjected to usual work-up including washing, drying and concentration to obtain 0.120 g of ethyl (E)-2-isopropyl-5-methyl-3,5-hexadienoate (96.3% GC, yield 78%) as the target compound. As a result of the GC analyses of the reaction mixture and the product, ethyl (Z)-2-isopropyl-5-methyl-3,5-hexadienoate, which was a geometric isomer of the target compound, was not detected. The product was the same as the product in Example 1.

Example 5

Synthesis Example 5 of Ethyl (E)-2-isopropyl-5-methyl-3,5-hexadienoate Corresponding to General Formula (2) in which Ra is an Ethyl Group (CH$_3$CH$_2$, Et)

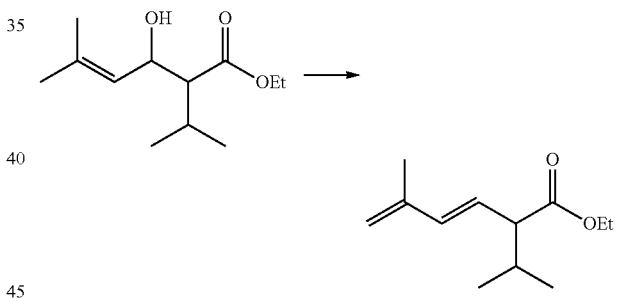

Under a nitrogen atmosphere, 10 ml of 20% hydrochloric acid was added to a mixture of 625 mg of ethyl 3-hydroxy-2-isopropyl-5-methyl-4-hexenoate, 10 ml of ethyl acetate and 20 ml of diethyl ether, while the mixture was stirred at room temperature. The reaction progress was monitored by GC, while the mixture was stirred at room temperature. By identifying the compound by GC-MS analyses, ethyl 3-chloro-2-isopropyl-5-methyl-4-hexenoate and ethyl 5-hydroxy-2-isopropyl-5-methyl-3-hexenoate were observed at the initial stage of the reaction, but the reaction product was gradually converged to ethyl (E)-2-isopropyl-5-methyl-3,5-hexadienoate as the target compound. The reaction mixture was stirred at room temperature for 48 hours, and then the organic phase was separated. An aqueous sodium hydroxide solution was added to the aqueous phase to adjust the pH therein to 7, and the resulting mixture was extracted with diethyl ether. The combined organic phase was subjected to usual work-up including washing, drying and concentration to obtain 870 mg of ethyl (E)-2-isopropyl-5-methyl-3,5-hexadienoate (59.8% GC, yield 91%) as the target compound. As a result of the GC analyses of the reaction mixture and the product, ethyl (Z)-2-isopropyl-5-methyl-3,5-hexadienoate, which was a geometric isomer of the target compound, was not detected. The product was the same as the product in Example 1.

Example 6

Synthesis Example 6 of Ethyl (E)-2-isopropyl-5-methyl-3,5-hexadienoate Corresponding to General Formula (2) in which Ra is an Ethyl Group (CH$_3$CH$_2$, Et)

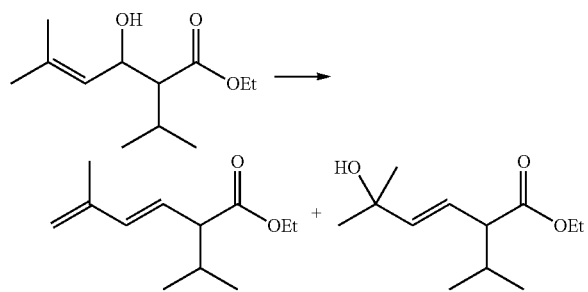

Under a nitrogen atmosphere, a mixture of 15 mg of ethyl 3-hydroxy-2-isopropyl-5-methyl-4-hexenoate and 2 mg of potassium hydrogen sulfate was stirred at 70° C. for 4 hours, and then at room temperature for 3 days. The reaction was monitored by GC and structures were analyzed by GC-MS. At the time when 2.5% of ethyl 3-hydroxy-2-isopropyl-5-methyl-4-hexenoate as the raw material remained, 29.3% of ethyl (E)-2-isopropyl-5-methyl-3,5-hexadienoate as the target compound and 23.6% of ethyl (E)-5-hydroxy-2-isopropyl-5-methyl-3-hexenoate were formed as main products. The result suggests that the reaction proceeded through a carbocation intermediate having a cation at the 5-position.

Ethyl (E)-2-isopropyl-5-methyl-3,5-hexadienoate

GC-MS (EI, 70 eV): 41, 53, 67, 81 (base peak), 111, 123, 139, 154, 181, 196 (M$^+$).

Ethyl (E)-5-hydroxy-2-isopropyl-5-methyl-3-hexenoate

GC-MS (EI, 70 eV): 43, 55, 69, 81, 97, 111, 125, 139, 153, 171, 199, 214 (M$^+$).

Example 7

Synthesis example 7 of ethyl (E)-2-isopropyl-5-methyl-3,5-hexadienoate Corresponding to General Formula (2) in which Ra is an Ethyl Group (CH$_3$CH$_2$, Et)

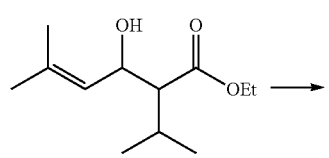

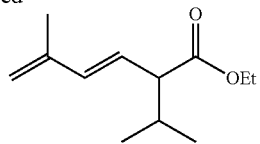

Under a nitrogen atmosphere, a mixture of 670 mg of ethyl 3-hydroxy-2-isopropyl-5-methyl-4-hexenoate and 15 ml of benzene was added to a mixture of 250 mg of diphosphorus pentoxide and 50 ml of benzene, while the latter mixture was stirred with heating at 40 to 50° C. The reaction mixture was refluxed with stirring for 3 hours. The reaction mixture was cooled to room temperature, and then water was added thereto. The separated organic phase was subjected to usual work-up including washing, drying and concentration to obtain 790 mg of ethyl (E)-2-isopropyl-5-methyl-3,5-hexadienoate (72.1% GC, yield 93%) as the target compound. As a result of the GC analyses of the reaction mixture and the product, ethyl (Z)-2-isopropyl-5-methyl-3,5-hexadienoate, which was a geometric isomer of the target compound, was not detected. The product was the same as the product in Example 1.

As shown in the following reaction scheme, it has been reported that ethyl 3-hydroxy-2,5-dimethyl-4-hexenoate as the raw material is dehydrated in the same conditions as in this example to obtain ethyl 2,5-dimethyl-2,4-hexadienoate (see Inoue, Kagaku no Ryoiki, 9, 531 (1955) and Inoue et al., Bochu Kagaku, 20, 102 (1955) in which the stereochemistries of the raw material and the product are not described). This experiment reveals that the difference in the substituents at the 2-position results in different selectivity.

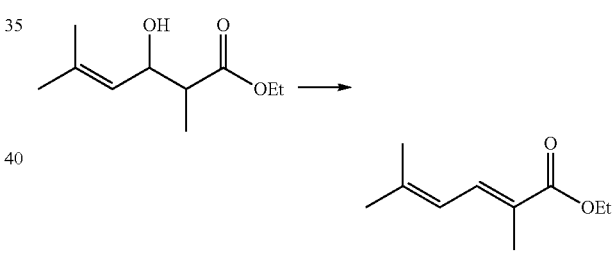

Example 8

Synthesis Example 1 of methyl (E)-2-isopropyl-5-methyl-3,5-hexadienoate Corresponding to General Formula (2) in which Ra is a Methyl Group (CH$_3$, Me)

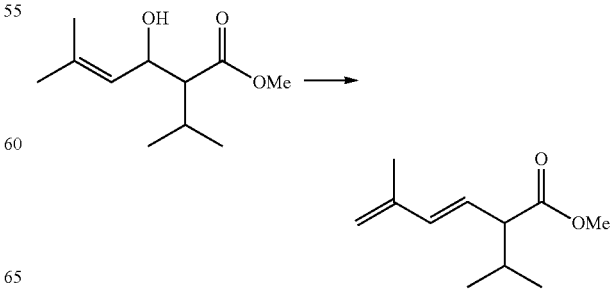

Methyl (E)-2-isopropyl-5-methyl-3,5-hexadienoate (yield 92%) was obtained as the target compound by the same reaction as in Example 7 except that methyl 3-hydroxy-2-isopropyl-5-methyl-4-hexenoate was used in the place of ethyl 3-hydroxy-2-isopropyl-5-methyl-4-hexenoate.

Methyl (E)-2-isopropyl-5-methyl-3,5-hexadienoate

Colorless Oil
IR (D-ATR): ν=2961, 2873, 1737, 1435, 1240, 1154, 969, 888 cm$^{-1}$.
$^1$H-NMR (500 MHz, CDCl$_3$): δ=0.87 (31H, d, J=6.9 Hz), 0.92 (3H, d, J=6.5 Hz), 1.84 (3H, s), 1.95-2.06 (1H, m), 2.74 (1H, t, J=9.1 Hz), 3.67 (3H, s), 4.93 (1H, br. s), 4.94 (1H, br. s), 5.61 (1H, dd, J=9.6, 15.7 Hz), 6.18 (1H, d, J=15.7 Hz) ppm.
$^{13}$C-NMR (125 MHz, CDCl$_3$): δ=18.56, 19.83, 20.75, 31.18, 51.55, 57.09, 116.23, 126.63, 135.97, 141.50, 174.46 ppm.
GC-MS (EI, 70 eV): 41, 53, 67, 81 (base peak), 91, 107, 125, 140, 182 (M$^+$).
GC-MS (CI, isobutane): 115, 123, 183 [(M+H)$^+$].

Example 9

Synthesis Example 2 of Methyl (E)-2-isopropyl-5-methyl-3,5-hexadienoate Corresponding to General Formula (2) in which Ra is a Methyl Group (CH$_3$, Me)

Example 9-1

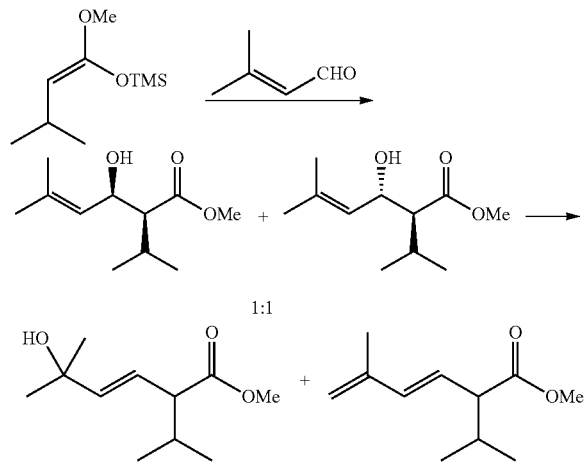

Under a nitrogen atmosphere, 11.62 g of silicon tetrachloride (SiCl$_4$) was added to a mixture of 14.0 g of 3-methyl-1-methoxy-1-trimethylsilyloxy-1-butene as a silyl ketene acetal that had been synthesized from methyl isovalerate by a usual method, 100 ml of methylene chloride and 1.04 ml of hexamethylphosphoric triamide (HMPA), while the mixture was stirred at −70° C., and the reaction mixture was stirred at −70° C. for 15 minutes. Next, a mixture of 5.10 g of 3-methyl-2-butenal and 10 ml of methylene chloride was added thereto, and the reaction mixture was further stirred at −70° C. for 2 hours, and then cooled on ice for 2 hours. It was found by GC-MS analyses of the reaction mixture that a syn-isomer and an anti-isomer of methyl 3-hydroxy-2-isopropyl-5-methyl-4-hexenoate were formed at a ratio of 48:52.

One Isomer of Methyl 3-hydroxy-2-isopropyl-5-methyl-4-hexenoate

The GC retention time was 5.00 min. As for GC conditions, a gas chromatograph of Shimazdu GC-14A with a column of 5% Ph-Me silicone having 0.25 mm φ×25 m, a carrier gas of helium, and flame ionization detector (FID) were used.
GC-MS (EI, 70 eV): 41, 55, 69, 85 (base peak), 101, 116, 157, 185, 200 (M$^+$).

The Other Isomer of Methyl 3-hydroxy-2-isopropyl-5-methyl-4-hexenoate

The GC retention time was 5.81 min. As for GC conditions, a gas chromatograph of Shimazdu GC-14A with a column of 5% Ph-Me silicone having 0.25 mm φ×25 m, a carrier gas of helium, and flame ionization detector (FID) were used.
GC-MS (EI, 70 eV): 41, 55, 69, 85 (base peak), 101, 116, 157, 185, 200 (M$^+$).

The reaction mixture was subjected to dropwise addition of 150 ml of water, while the mixture was cooled on ice, so that the reaction system became acidic due to hydrochloric acid generated by the reaction of water and silicon tetrachloride, and then stirred at room temperature for 18 hours. The resulting precipitate was removed by filtration, and water and diethyl ether were added to the filtrate. The separated organic phase was subjected to usual work-up including washing, drying and concentration to obtain 13.18 g of crude product. The 12.0 g of the crude product was purified by silica gel column chromatography to obtain 2.31 g of methyl (E)-2-isopropyl-5-methyl-3,5-hexadienoate as the target compound (91.9% GC, yield 21%, the compound was the same as the target compound in Example 8) and to obtain 8.11 g of methyl (E)-5-hydroxy-2-isopropyl-5-methyl-3-hexenoate (97.8% GC, yield 71%). The geometries of the double bonds of these compounds were determined by the fact that the $^1$H-$^1$H coupling constant J between the 3- and 4-positions was 15.7 Hz in $^1$H-NMR as shown below. As a result of the GC analyses of the reaction mixture and the product, methyl (Z)-2-isopropyl-5-methyl-3,5-hexadienoate and methyl (Z)-5-hydroxy-2-isopropyl-5-methyl-3-hexenoate, which are geometric isomers of the target compounds, were not detected.

Methyl (E)-5-hydroxy-2-isopropyl-5-methyl-3-hexenoate

Colorless Oil
IR (D-ATR): ν=3464, 2968, 2934, 2874, 1737, 1722, 1435, 1370, 1244, 1195, 1153, 975 cm$^{-1}$.
$^1$H-NMR (500 MHz, CDCl$_3$): δ=0.85 (3H, d, J=6.9 Hz), 0.88 (3H, d, J=6.9 Hz), 1.29 (3H, s), 1.79 (1H, br.), 1.91-2.01 (1H, m), 2.65 (1H, t-like, J=8.8 Hz), 3.65 (3H, s), 5.61 (1H, dd, J=9.1, 15.7 Hz), 5.67 (1H, d, J=15.7 Hz) ppm.
$^1$H-NMR decoupling: The decoupling by irradiation of H at 2-position appearing at δ=2.65 changed H at 3-position appearing at δ=5.61 into triplet having J=15.7 Hz. This indicates that the $^1$H-$^1$H coupling constant J between the 3-position and the 4-position is 15.7 Hz.

$^{13}$C-NMR (125 MHz, CDCl$_3$): δ=19.65, 20.67, 29.57, 29.76, 30.88, 51.51, 56.41, 70.60, 123.43, 141.67, 174.59 ppm.

GC-MS (EI, 70 eV): 43, 55, 69, 81, 97, 111 (base peak), 125, 140, 153, 168, 185, 200 (M$^+$).

GC-MS (CI, isobutane): 183 [(M+H−H$_2$O)$^+$].

Example 9-2

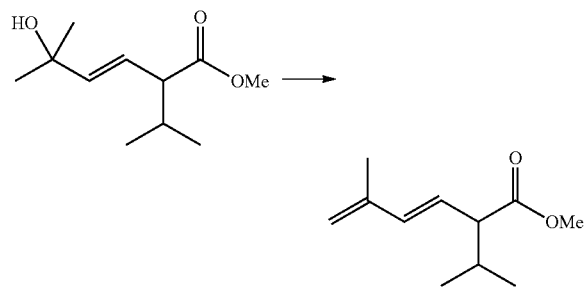

Under a nitrogen atmosphere, 1.20 g of methanesulfonyl chloride was added to a mixture of 1.65 g of methyl (E)-5-hydroxy-2-isopropyl-5-methyl-3-hexenoate (97.8% GC), 20 ml of tetrahydrofuran and 5 ml of trimethylamine, while the mixture was cooled on ice, and then the reaction mixture was stirred at room temperature for 17 hours. The reaction mixture was poured into water and was extracted with n-hexane. The separated organic phase was subjected to usual work-up including washing, drying and concentration to obtain 0.96 g of methyl (E)-2-isopropyl-5-methyl-3,5-hexadienoate (84.5% GC, yield 91%) as the target compound. The product was also the same as the product in Example 8.

Example 10

Synthesis Example of Isobutyl (E)-2-isopropyl-5-methyl-3,5-hexadienoate Corresponding to General Formula (2) in which Ra is (CH$_3$)$_2$CHCH$_2$

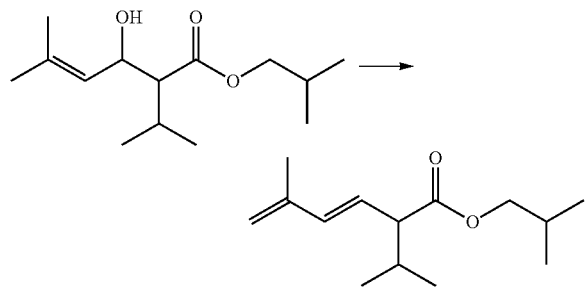

Isobutyl (E)-2-isopropyl-5-methyl-3,5-hexadienoate (yield 88%) was obtained as the target compound by the same reaction as in Example 1 except that isobutyl 3-hydroxy-2-isopropyl-5-methyl-4-hexenoate was used instead of ethyl 3-hydroxy-2-isopropyl-5-methyl-4-hexenoate.

Isobutyl (E)-2-isopropyl-5-methyl-3,5-hexadienoate

Yellow Oil

IR (D-ATR): ν=2962, 2874, 1733, 1469, 1370, 1284, 1234, 1151, 1006, 968 cm$^{-1}$.

$^1$H-NMR (500 MHz, CDCl$_3$): δ=0.88 (3H, d, J=6.9 Hz), 0.92 (3H, s), 0.93 (3H, s), 0.93 (3H, d, J=6.5 Hz), 1.84 (3H, s), 1.88-1.98 (1H, m), 1.98-2.07 (1H, m), 2.74 (1H, t, J=9.1 Hz), 3.81-3.91 (2H, m), 4.92 (1H, br. s), 4.93 (1H, br. s), 5.63 (1H, dd, J=9.5, 15.7 Hz), 6.18 (1H, d, J=15.7 Hz) ppm.

$^{13}$C-NMR (125 MHz, CDCl$_3$): δ=18.57, 19.05, 19.04, 19.87, 20.78, 27.70, 31.15, 57.38, 70.49, 116.07, 126.90, 135.82, 141.56, 174.02 ppm.

GC-MS (EI, 70 eV): 29, 41, 57, 81 (base peak), 93, 111, 123, 153, 168, 224 (M$^+$).

GC-MS (CI, isobutane): 123, 169, 225 [(M+H)$^+$].

Example 11

Synthesis Example of benzyl (E)-2-isopropyl-5-methyl-3,5-hexadienoate Corresponding to General Formula (2) in which Ra is C$_6$H$_5$CH$_2$

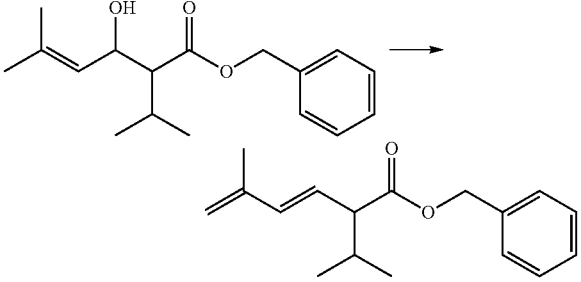

Benzyl (E)-2-isopropyl-5-methyl-3,5-hexadienoate (yield 88%) was obtained as the target compound by the same reaction as in Example 3 except that benzyl 3-hydroxy-2-isopropyl-5-methyl-4-hexenoate was used instead of ethyl 3-hydroxy-2-isopropyl-5-methyl-4-hexenoate.

Benzyl (E)-2-isopropyl-5-methyl-3,5-hexadienoate

Colorless Oil

IR (D-ATR): ν=3032, 2962, 2872, 1732, 1455, 1231, 1214, 1148, 970 cm$^{-1}$.

$^1$H-NMR (500 MHz, CDCl$_3$): δ=0.89 (3H, d, J=6.9 Hz), 0.93 (3H, d, J=6.5 Hz), 1.86 (3H, s), 2.00-2.11 (1H, m), 2.81 (1H, t, J=9.0 Hz), 4.94 (1H, br. s), 4.96 (1H, br. s), 5.11 (1H, d, J=12.2 Hz), 5.16 (1H, d, J=12.2 Hz), 5.66 (1H, dd, J=9.6, 15.7 Hz), 6.21 (1H, d, J=15.3 Hz), 7.30-7.40 (5H, m) ppm.

$^{13}$C-NMR (125 MHz, CDCl$_3$): δ=18.55, 19.81, 20.72, 31.20, 57.11, 66.14, 116.24, 126.51, 128.06, 128.10, 128.46, 136.00, 136.08, 141.50, 173.80 ppm.

GC-MS (EI, 70 eV): 43, 65, 81, 91 (base peak), 107, 123, 258 (M$^+$).

[II] Synthesis of (E)-2-Isopropyl-5-Methyl-3,5-Hexadienol represented by General Formula (3)

Example 12

Synthesis Example of (E)-2-isopropyl-5-methyl-3,5-hexadienol

Under a nitrogen atmosphere, a mixture of 7.98 g of ethyl (E)-2-isopropyl-5-methyl-3,5-hexadienoate (84.2% GC)

obtained in Example 1 and 40 ml of tetrahydrofuran was added dropwise to a mixture of 2.23 g of lithium aluminum hydride and 50 ml of tetrahydrofuran, while the latter mixture was cooled on ice. The reaction mixture was stirred for 100 minutes, while cooled on ice. The reaction mixture was subjected to sequential additions of 2.23 g of water, 2.23 g of 15% aqueous sodium hydroxide solution, and 6.69 g of water, while the mixture was still cooled on ice. After the completion of heat generation, the temperature of the reaction mixture was increased to room temperature with stirring. The resulting precipitate was filtered off, and the filtrate was concentrated under reduced pressure to obtain 6.23 g of the target compound (85.3% GC, quantitative yield).

(E)-2-Isopropyl-5-methyl-3,5-hexadienol

Colorless Oil

IR (D-ATR): ν=3350, 2958, 2929, 2873, 1609, 1464, 1386, 1368, 1061, 1037, 968 cm$^{-1}$.

$^1$H-NMR (500 MHz, CDCl$_3$): δ=0.86 (3H, d, J=6.9 Hz), 0.91 (3H, d, J=6.9 Hz), 1.48-1.55 (1H, br.), 1.65-1.75 (1H, m), 1.85 (3H, s), 2.02-2.09 (1H, m), 3.46 (1H, br. t-like, J=10 to 11 Hz), 3.65-3.72 (1H, m), 4.92 (2H, br. s), 5.44 (1H, dd, J=9.6, 15.7 Hz), 6.22 (1H, d, J=15.7 Hz) ppm.

$^{13}$C-NMR (125 MHz, CDCl$_3$): δ=18.64, 19.57, 20.82, 29.00, 52.58, 64.22, 115.55, 129.46, 136.35, 141.56 ppm.

GC-MS (EI, 70 eV): 41, 55, 67, 81 (base peak), 93, 109, 123, 139, 154 (M$^+$).

These spectral data were in good agreement with those in J. Tabata et al., J. Chem. Ecol., 41, 194 (2015).

[III] Synthesis of
(E)-2-Isopropyl-5-Methyl-3,5-Hexadienyl Carboxylate Represented by General Formula (4)

Example 13

Synthesis Example of (E)-2-isopropyl-5-methyl-3,5-hexadienyl acetate corresponding to General Formula (4) in which Rb is a Methyl Group (CH$_3$)

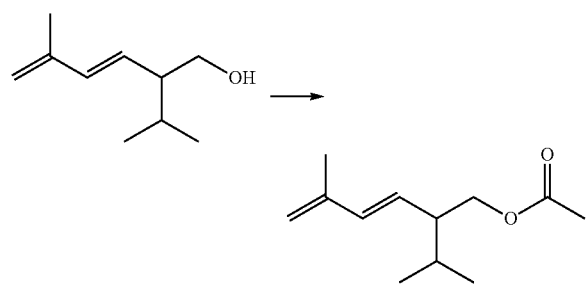

Under a nitrogen atmosphere, 9.90 g of acetic anhydride was added to a mixture of 5.92 g of (E)-2-isopropyl-5-methyl-3,5-hexadienol (85.3% GC), 24 ml of pyridine and 50 ml of ethyl acetate, while the mixture was stirred and cooled on ice. The reaction mixture was stirred at room temperature for 16 hours, and then was poured into a saturated aqueous sodium hydrogen carbonate solution. The separated organic phase was subjected to usual work-up including washing, drying and concentration to obtain 7.41 g of a crude product of the target (E)-2-isopropyl-5-methyl-3,5-hexadienyl acetate (83.6% GC, yield 97%). The crude product was purified by silica gel column chromatography to obtain Fraction 1 containing 4.59 g of (E)-2-isopropyl-5-methyl-3,5-hexadienyl acetate (94.5% GC) and Fraction 2 containing 2.06 g of the same compound (78.7% GC) as the target compound (total yield 93%). Fraction 1 was further purified by vacuum distillation to obtain 1.30 g of (E)-2-isopropyl-5-methyl-3,5-hexadienyl acetate (93.5% GC) and 3.15 g of the same compound (95.7% GC) as the target compound.

(E)-2-Isopropyl-5-methyl-3,5-hexadienyl Acetate

Colorless Oil

Boiling point: 56 to 59° C./400 Pa

IR (D-ATR): ν=2960, 2874, 1742, 1464, 1382, 1368, 1234, 1034, 969 cm$^{-1}$.

$^1$H-NMR (500 MHz, CDCl$_3$): δ=0.86 (3H, d, J=6.9 Hz), 0.91 (3H, d, J=6.5 Hz), 1.72-1.80 (1H, m), 1.82 (3H, s), 2.01 (3H, s), 2.20-2.27 (1H, m), 4.08 (2H, d, J=6.9 Hz), 4.89 (2H, br. s), 5.44 (1H, dd, J=9.2, 15.7 Hz), 6.14 (1H, d, J=15.7 Hz) ppm.

$^{13}$C-NMR (125 MHz, CDCl$_3$): δ=18.61, 18.89, 20.68, 20.94, 28.06, 48.26, 65.95, 115.19, 128.48, 135.32, 141.81, 171.11 ppm.

GC-MS (EI, 70 eV): 43, 55, 67, 79, 93, 107, 121 (base peak), 136, 196 (M$^+$).

GC-MS (CI, isobutane): 81, 137 [(M+H)$^+$].

These spectral data were in good agreement with those in J. Tabata et al., J. Chem. Ecol., 41, 194 (2015).

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:
1. An (E)-2-isopropyl-5-methyl-3,5-hexadienoate compound corresponding to General Formula (2):

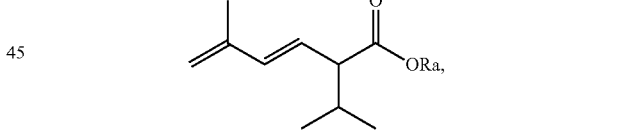

wherein Ra is a monovalent hydrocarbon group having 1 to 10 carbon atoms.

2. A method for producing the (E)-2-isopropyl-5-methyl-3,5-hexadienoate compound of claim 1, the method comprising:
a step of dehydrating a 3-hydroxy-2-isopropyl-5-methyl-4-hexenoate compound corresponding to General Formula (1):

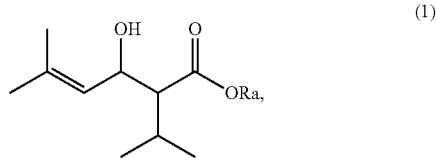

wherein Ra is a monovalent hydrocarbon group having 1 to 10 carbon atoms, to obtain the (E)-2-isopropyl-5-methyl-3,5-hexadienoate compound.

3. A method for producing (E)-2-isopropyl-5-methyl-3,5-hexadienol, the method comprising:
 a step of reducing an alkoxycarbonyl group of the (E)-2-isopropyl-5-methyl-3,5-hexadienoate compound of claim 1 to obtain the (E)-2-isopropyl-5-methyl-3,5-hexadienol corresponding to Formula (3):

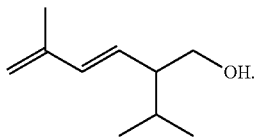

(3)

4. A method for producing an (E)-2-isopropyl-5-methyl-3,5-hexadienyl carboxylate compound, the method comprising the steps of:
 reducing an alkoxycarbonyl group of the (E)-2-isopropyl-5-methyl-3,5-hexadienoate compound of claim 1 to obtain (E)-2-isopropyl-5-methyl-3,5-hexadienol corresponding to Formula (3):

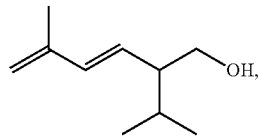

(3)

and
 esterifying the (E)-2-isopropyl-5-methyl-3,5-hexadienol (3) to obtain the (E)-2-isopropyl-5-methyl-3,5-hexadienyl carboxylate compound corresponding to General Formula (4):

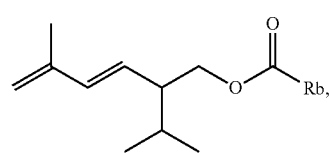

(4)

wherein Rb is a monovalent hydrocarbon group having 1 to 10 carbon atoms.

* * * * *

UNITED STATES PATENT AND TRADEMARK OFFICE
CERTIFICATE OF CORRECTION

PATENT NO. : 9,725,400 B2
APPLICATION NO. : 15/219655
DATED : August 8, 2017
INVENTOR(S) : Kinsho et al.

It is certified that error appears in the above-identified patent and that said Letters Patent is hereby corrected as shown below:

On the Title Page

Item (56) References Cited, Publications, Simon et al. cite:
Please correct "Synthes: von d,l-β,y-Dihydro-lavandulol" to read -- Synthese von d,l-β,γ-Dihydro-lavandulol --

In the Specification

Column 7, Line 30, syn-(1):

Please correct " 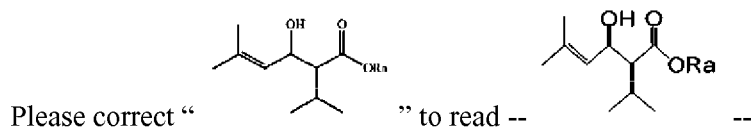 " to read -- --

Column 7, Line 35, anti-(1):

Please correct " 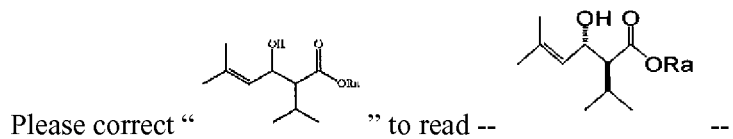 " to read -- --

Column 21, Line 21:
Please correct "31H" to read -- 3H --

Column 27, Line 12:
Please correct "31H" to read -- 3H --

Column 30, Line 6:
Please correct "31H" to read -- 3H --

Signed and Sealed this
Twenty-sixth Day of June, 2018

Andrei Iancu
*Director of the United States Patent and Trademark Office*